United States Patent [19]

Mase et al.

[11] Patent Number: 4,670,128
[45] Date of Patent: Jun. 2, 1987

[54] ELECTROCHEMICAL DEVICE

[75] Inventors: Syunzo Mase, Aichi; Shigeo Soejima, Nagoya, both of Japan

[73] Assignee: NGK Insulators, Ltd., Japan

[21] Appl. No.: 783,575

[22] Filed: Oct. 3, 1985

Related U.S. Application Data

[62] Division of Ser. No. 670,879, Nov. 13, 1984, Pat. No. 4,579,643.

[30] Foreign Application Priority Data

Nov. 18, 1983 [JP] Japan ................................. 58-218400
Jun. 6, 1984 [JP] Japan ................................. 59-116225
Sep. 3, 1984 [JP] Japan ................................. 59-183957

[51] Int. Cl.[4] ............................................. G01N 27/58
[52] U.S. Cl. ................................. 204/427; 204/426; 204/425; 204/424
[58] Field of Search ............... 204/412, 421, 424, 425, 204/426, 427, 428, 429, 408

[56] References Cited

U.S. PATENT DOCUMENTS

| | | | |
|---|---|---|---|
| 4,088,543 | 5/1978 | Ruka ................................. | 204/429 |
| 4,107,019 | 8/1978 | Takao et al. ........................ | 204/426 X |
| 4,158,166 | 6/1979 | Isenberg ........................... | 204/412 X |
| 4,272,329 | 6/1981 | Hetrick et al. ..................... | 204/1 T |
| 4,282,080 | 8/1981 | Muller et al. ...................... | 204/412 |
| 4,292,158 | 9/1981 | Muller et al. ...................... | 204/426 |
| 4,298,573 | 11/1981 | Fujishiro .......................... | 204/426 |
| 4,300,990 | 11/1981 | Maurer ............................. | 204/412 |
| 4,334,974 | 6/1982 | Muller et al. ...................... | 204/412 |
| 4,416,763 | 11/1983 | Fujishiro .......................... | 204/412 |
| 4,428,817 | 1/1984 | Isenberg ........................... | 324/29 |
| 4,450,065 | 5/1984 | Yamada et al. ..................... | 204/412 |
| 4,505,806 | 3/1985 | Yamada ............................ | 204/426 X |
| 4,505,807 | 3/1985 | Yamada ............................ | 204/426 X |
| 4,541,899 | 9/1985 | Mase et al. ........................ | 204/426 X |

Primary Examiner—John F. Niebling
Assistant Examiner—Nam X. Nguyen
Attorney, Agent, or Firm—Parkhurst & Oliff

[57] ABSTRACT

An electrochemical device comprising at least one electrochemical cell having a planar solid electrolyte body, and a first and a second electrode one of which is disposed on the solid electrolyte body. The device has a measurement-gas space communicating with an outside space for introducing a measurement gas, and a reference-gas space into which a reference gas is introduced. The first and second electrodes are exposed to the measurement-gas and reference-gas spaces, respectively. The measurement gas is introduced into the measurement-gas space with a diffusion resistance to molecules of a selected component of the measurement gas. The measurement-gas and reference-gas spaces are juxtaposed in spaced-apart relation with each other in substantially the same plane parallel to the planar solid electrolyte body. The device may include two electrochemical cells, on serving as a sensing cell having said first and second electrodes, and the other serving as a pumping cell haivng two electrodes one of which is exposed to the measurement-gas space. A heating layer may be disposed on the side of the sensing cell. In this case, the first and second electrodes are spaced from each other in the direction parallel to the solid electrolyte body.

8 Claims, 20 Drawing Figures

ELECTROCHEMICAL DEVICE

This is a division of application Ser. No. 670,879 filed Nov. 13, 1984, now U.S. Pat. No. 4,579,643.

BACKGROUND OF THE INVENTION

The present invention relates in general to an electrochemical device, and more particularly to improvements in an electrochemical device of laminar structure which includes an electrochemical cell using a planar solid electrolyte body.

There have been known various electrochemical devices using solid electrolyte, for example, oxygen sensors to detect the oxygen concentration of an exhaust gas emitted from internal combustion engines of automotive vehicles. The typical examples of such oxygen sensors include an oxygen sensor which comprises a body of oxygen-ion conductive solid electrolyte such as zirconia ceramics and which operates to determine the oxygen concentration according to the principle of an oxygen concentration cell. Also known in the art are electrochemical devices such as sensing and pumping elements for detecting hydrogen, nitrogen, carbon dioxide, etc. In such electrochemical devices, solid electrolyte materials have been generally used in the form of a tubular body which has an elongate bore closed at its one end. In recent years, however, it has been attempted to replace the tubular solid electrolyte body with a solid electrolyte body of planar shape, as disclosed in U.S. Pat. Nos: 4,334,974; 4,282,080; and 4,300,990, in view of relatively low productivity and high cost of manufacture of solid electrolyte bodies of tubular type, and from the standpoint of easy assembling of parts with a planar solid electrolyte body. When such planar solid electrolyte bodies are employed, suitable electrodes are disposed on the surfaces of the planar body or layer of solid electrolyte, and the electrolyte bodies and other parts are assembled in stack into a laminar structure constituting an electrochemical cell or sensing element.

As indicated above, such an electrochemical cell of laminar structure is usually constituted by a planar solid electrolyte body and two (a pair of) electrodes. This laminar structure is provided with an internal cavity or chamber into which a gas to be measured (hereinafter referred to as "measurement gas") such as an exhaust gas is introduced. The laminar structure is further provided with an internal space, more specifically, a reference-gas passage in which is introduced a reference substance used as a reference for the measurement gas for measuring an electromotive force induced between the two electrodes. These cavity and reference-gas space or passage are formed so as to extend parallel to the surfaces of the electrodes, but disposed in spaced-apart relation with each other in the direction of the thickness of the cell (in the direction of lamination of the device), and therefore increase the thickness of the cell.

A study by the inventors revealed that an electrochemical sensor using such a thick cell tends to have a relatively large temperature gradient in the direction of thickness, particularly when its solid electrolyte body is heated, by a suitable heater, to an elevated temperature for accurate and reliable operation of the cell, and consequently the solid electrolyte body is likely to be damaged due to thermal stress caused by such a large temperature gradient. In addition to this problem, the inventors found that the large thickness of the cell is a potential factor for an increase in time required for the solid electrolyte body to be heated to its operating temperature. Although electrochemical cells of planar laminar type are advantageous for its relatively compact structure, as compared with a conventional cell of tubular type, there is a growing need of minimizing the size of the planar electrochemical cells, to meet the recent trend in this field of industry that the electrochemical cells are increasingly employed for automotive vehicles as oxygen sensors for sensing oxygen in exhaust gases from the engines.

As indicated above, it is usually preferred that the electrodes and solid electrolyte body constituting an electrochemical cell of the electrochemical device are heated by a suitable heater to an elevated temperature in order to assure an efficient, accurate operation of the electrochemical cell while the temperature of a gas to be measured is relatively low. For this reason, a known electrochemical device is provided with a heater, i.e., a heating layer, which is disposed adjacent to an electrochemical cell consisting of a solid electrolyte body and electrodes, such that an insulating layer is interposed between the heater and the electrochemical cell. Alternatively, a heater is disposed at a position spaced from the electrodes in the same plane of the electrochemical cell.

By the way, one example of electrochemical devices of laminar structure as indicated above, includes an electrochemical pumping cell which has two porous electrodes disposed on opposite surfaces of a porous solid electrolyte layer, and an electrochemical sensing cell which has two porous elecrtrodes disposed on another solid electrolyte layer. These pumping and sensing cells are assembled in stack into an electrochemical device of laminar structure. This kind of device is known to be useful as a sensor having a wide measurement range. In the case where such an electrochemical device is provided with a heater as previously indicated, the heater is generally disposed on the side of the sensing cell. If a heater is disposed on the side of the pumping cell, a pattern of heating element located over the pumping electrodes will tend to excessively heat the electrodes and cause local unevenness in diffusion of a measurement gas through the pumping cell, and may consequently reduce the accuracy of measurement of the device. In the case where the heating element is not disposed over the electrodes, but located sideways of the electrodes to heat them in the lateral directions, the temperature of the heated electrodes is liable to be varied from one area to another, causing local unevenness in amount of flow of a pumping current through the cell. This may also be a cause for lowering the measuring accuracy of the electrochemical device.

However, when a heater is disposed on the side of an electrochemical sensing cell, this sensing cell is interposed between the heating element and the electrodes of a pumping cell. The interposition of the sensing cell permits better distribution of heat over the pumping cell. Further, this arrangement will not hinder the diffusion of the measurement gas through the pumping cell. On the other hand, the interposition of the sensing cell between the pumping cell and the heater inherently results in insufficient heating of the pumping cell by the heater, and therefore the use of the heater does not necessarily contribute to improvement in the pumping ability of the pumping cell. In the light of this disadvantage, it is considered to use a heater having a larger heating capacity for generation of an increased amount of heat. Such a solution, however, may lead to shortening of the service life of the heating layer of the electrochemical device.

SUMMARY OF THE INVENTION

The present invention was developed in the light of the above situations in the prior art. It is therefore an object of the present invention to provide a compact electrochemical device including an electrochemical cell which has a reduced thickness and consequently a reduced temperature gradient in the direction of thickness.

Another object of the invention is the provision of such an electrochemical device including heater which efficiently heats the device in a shorter period of time to its operating temperature, with even heat distribution through the electrochemical cell.

A further object of the invention is to provide an electrochemical device equipped with such a heater, which assures efficient heat transfer from the heater to an electrochemical pumping cell for improvement in its pumping ability, and which is adapted for prolonged service life of the heater.

According to the invention, there is provided an electrochemical device for determining the concentration of a component of a gaseous fluid, comprising: (a) at least one electrochemical cell having a planar solid electrolyte body, and a first and a second electrode, at least one of the first and second electrodes being disposed on the planar solid electrolyte body; (b) means defining a measurement-gas space communicating with an outside space in which the gaseous fluid exists, the first electrode being exposed to the measurement-gas space; (c) diffusion-resistance means for communication between the outside space and the measurement-gas space, having a predetermined diffusion resistance to molecules of the component of the gaseous fluid, the component being diffused through the diffusion-resistance means into the measurement-gas space; and (d) means defining a reference-gas space in which a reference gas exists, the second electrode being exposed to the reference-gas space, the measurement-gas space and the reference-gas space being juxtaposed in spaced-apart relation with each other in substantially the same plane parallel to the surface of the planar solid electrolyte body.

In the electrochemical device of the invention constructed as described above, the measurement-gas space to which the measurement fluid (a gas in particular) is introduced, and the reference-gas space, are disposed so that they are spaced from each other in the direction along the surface of the planar solid electrolyte body, and located at substantially the same level parallel to the planar solid electrolyte body. Hence, the thickness of the electrochemical cell is reduced to a large extent, and the temperature gradient in the direction of the thickness is accordingly reduced, whereby the damage to the solid electrolyte body due to thermal stress is effectively restrained.

According to a preferred form of the invention, a heater layer incorporating a heating element is provided to heat said at least one electrochemical cell, in view of the fact that the electrochemical cell is not operated with a satisfactory performance while the temperature of the measurement fluid is low and the solid electrolyte body is not maintained at a sufficiently high temperature. As previously indicated, the reduced thickness of the electrochemical cell according to the invention results in a considerably reduced thickness of the electrochemical device including the cell, and therefore permits uniform heating of the cell by the heater layer to its operating temperature in a shorter time, thereby providing a highly appreciable advantage in thermal efficiency.

According to one embodiment of the invention, the diffusion-resistance means comprises means for defining an aperture communicating with the outside space and the measurement-gas space. In this instance, the aperture has a small diameter selected to provide the predetermined diffusion resistance.

According to another embodiment of the invention, the measurement-gas space is a thin flat space having a small depth as measured perpendicularly to the plane in which the measurement-gas and reference-gas spaces are juxtaposed. The depth of the thin flat space is selected so as to provide the predetermined diffusion resistance. In this case, the thin flat space serves as the diffusion-resistance means.

According to a further embodiment of the invention, the diffusion-resistance means comprises a porous layer disposed so as to define one side of the measurement-gas space. In this arrangement, the porous layer has a porosity selected to provide the predetermined diffusion resistance.

In accordance with one form of the above embodiments, the electrochemical device comprises two electrochemical cells one of which has the first and second electrodes and serves as an electrochemical sensing cell wherein an electromotive force between the first and second electrodes is measured. The other electrochemical cell serves as a pumping cell which has another planar solid electrolyte body, a third electrode, and a fourth electrode which is exposed to the measurement-gas space. One of the third and fourth electrodes is disposed on said another solid electrolyte body.

In the above instance, a single common electrode may serve as the first electrode of the electrochemical sensing cell and as the fourth electrode of the electrochemical pumping cell. In this case, it is possible to measure an electromotive force generated due to difference in concentration of the measurement component between the common electrode and the second electrode.

According to a preferred embodiment of the invention, a planar spacer member is provided, which has the measurement-gas and reference-gas spaces and which is interposed between the planar solid electrolyte bodies of the sensing and pumping cells.

According to an advantageous embodiment of the invention, the first electrode is covered with a porous ceramic protective layer, and contacted with the atmosphere in the measurement-gas space through this porous ceramic layer. In the case where the first electrode is used for a sensing cell, and the electrochemical device comprises a pumping cell, it is appreciated that the fourth electrode is also covered with a porous ceramic protective layer, and contacted with the atmosphere in the measurement-gas space through this another porous ceramic layer. In these preferred arrangements, the first electrode and/or fourth electrode are protected against direct contact with the measurement gas.

According to another advantageous aspect of the invention, there is provided an electrochemical device for determining the concentration of a component of a gaseous fluid, comprising: (a) an electrochemical pumping cell including a first solid electrolyte body of porous structure having a predetermined diffusion resistance to molecules of the component of the gaseous fluid, and an outer and an inner pumping electrode of porous structure disposed in alignment with each other on opposite surfaces of the first solid electrolyte body; (b) an electrochemical sensing cell including a second solid electrolyte body, a measuring and a reference electrode of porous structure disposed on the second solid electrolyte body, the measuring and reference electrodes being spaced from each other in a direction parallel to the surface of the second solid electrolyte body, the measuring electrode being aligned with the outer and inner pumping electrodes, the outer pumping electrode being exposed to the gaseous fluid, and the inner pumping electrode and the measuring electrodes being exposed to substantially the same atmosphere which is introduced from the gaseous fluid through the first porous solid electrolyte body, and which contains the component; (c) a heater layer incorporating a heating element, and disposed on one side of the second solid electrolyte body remote from the first solid electrolyte body, the heating element being located in alignment with the measuring electrode of the sensing cell; and (d) at least one gastight ceramic layer which substantially completely protects the reference electrode of the sensing cell from exposure to the component of the gaseous fluid.

In the electrochemical device constructed as described above, the reference electrode is spaced from the measuring electrode in the direction along the surface of the second solid electrolyte body, and the heating element of the heater is aligned with the measuring electrode. Therefore, the reference electrode will not intercept the heat from the heater toward the pumping electrodes of the pumping cell. Usually and preferably, a reference-gas passage is formed so that the reference electrode is exposed to a reference gas introduced in the reference-gas passage. In this instance, the spaced-apart arrangement of the reference electrode from the measuring electrode makes it possible to position the hating element in spaced relation with the reference-gas passage in the direction parallel to the surface of the second solid electrolyte body. Therefore, the heat transfer from the heating element toward the pumping electrodes will not be hindered by the reference-gas passage.

BRIEF DESCRIPTION OF THE DRAWING

The above and foregoing objects, features and advantages of the present invention will become more apparent from reading the following description of the preferred embodiments taken in conjunction with the accompanying drawings in which.

DETAILED DESCRIPTION OF THE PREFERRED EMBODIMENTS

Referring to the accompanying drawing illustrating preferred embodiments of the present invention, the arrangement of an electrochemical device suitable for implementation of the invention will be described in detail.

Figure 1:
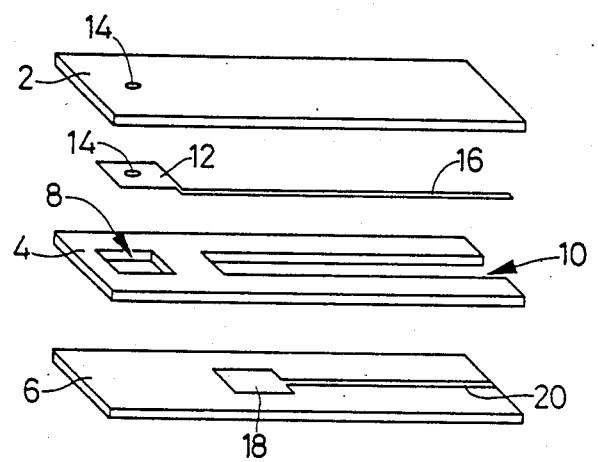
FIG. 1 is an exploded perspective view of a sensing element of one embodiment of an electrochemical device of the invention in the form of an oxygen sensor.

There is shown in the exploded perspective view of FIG. 1 a basic arrangement of a sensing element in one example of an oxygen sensor which is one embodiment of an electrochemical device of the invention. This oxygen sensor is of laminar structure which comprises three layers of solid electrolyte, i.e., first, second and third planar solid electrolyte bodies 2, 4 and 6 made of zirconia ceramics or the like. The second solid electrolyte body 4 has a rectangular cutout and an elongate slot which are closed at their upper and lower sides by the first and third planar solid electrolyte bodies 2 and 6. In other words, the second solid electrolyte body 4 cooperates with the first and third solid electrolyte bodies 2 and 6 to define a measurement-gas space and a reference-gas space, in the form of a rectangular cavity 8 and an elongate passage 10, respectively. These cavity and passage 8, 10 are spaced from each other in the direction along the surfaces of the planar solid electrolyte bodies and located in substantially the same plane parallel to the solid electrolyte bodies. This type of oxygen sensor is known as so-called "lean-burn" sensor.

The first electrolyte body 2 of the oxygen sensor has a first electrode 12 of porous structure made, for example, of platinum, on its inner surface, that is, on the surface not exposed to a measurement gas such as an exhaust gas. The first electrode 12 is exposed to the cavity 8, and connected through its lead 16 to a suitable external device. The first solid electrolyte body 2 and the first electrode 12 have apertures 14 serving as diffusion-resistance means, which have a small diameter selected to provide a predetermined diffusion resistance. For convenience, these apertures 14 will be treated as a single aperture 14 as needed, and serve as diffusion-resistance means as recited in the appended claims.

In the meantime, the third solid electrolyte body is provided with a second electrode 18 on the inner surface (on the surface opposite to the second solid electrolyte body 4), so that the second electrode 18 is exposed to the reference-gas passage 10. The second electrode 18 is connected through its lead 20 to a suitable external device.

In the electrochemical device with the above-described construction, the first electrode 12 functions not only as a pumping electrode, but also as a measuring electrode for sensing the measurement gas introduced in the measurement-gas cavity 8. The second electrode 18 serves as another pumping electrode, and also as a reference electrode which is contacted with a reference substance such as the ambient atmosphere introduced in the reference-gas passage 10. Stated more specifically, by applying a suitable voltage between the first and second electrodes 12 and 18, the oxygen sensor operates in the well known manner, to move the oxygen in the cavity 8 into the passage 10 primarily through the second solid electrolyte body 4, in the direction along the surface of the body 4. The amount of the oxygen to be moved toward the space 10 is varied in proportion to the amount of an electric current flowing through the electrodes. In the meantime, an electromotive force generated between the first and second electrodes 12, 18 is measured to determine the concentration of the oxygen of the measurement gas introduced through the aperture 14.

While the instant oxygen sensor is adapted to introduce a measurement gas, more specifically, its oxygen component into the cavity 8 through the aperture 14 by an oxygen pumping function performed by means of the first and second electrodes 12, 18, the rate of flow of the oxygen component through the aperture 14 is limited by the diameter of the aperture 14, whereby the oxygen partial pressure in the cavity 8 is made lower than that of the measurement gas. Consequently, the oxygen sensor is suitably used as a lean-burn sensor for controlling an engine which emanates an exhaust gas of lean air-fuel ratio whose oxygen partial pressure is higher than that of the stoichiometric air-fuel ratio.

However, the electrochemical device of the instant embodiment is also usable for determining the oxygen concentration of an equilibrated atmosphere such as an exhaust gas which is produced in combustion at the stoichiometric air-fuel ratio. In this case, an electromotive force between the first and second electrodes 12 and 18 is measured, but an oxygen pumping function by application of a DC voltage between the electrodes is not offered.

Further, the instant basic arrangement of the electrochemical device is also usable as a rich-burn sensor, more particularly, a sensor for detecting unburned components of such an exhaust gas that is produced in combustion at an air-fuel ratio in a fuel-rich range, which exhaust gas has an oxygen partial pressure lower than that of the stoichiometric air-fuel ratio and contains the unburned components in relatively large amounts. In this case, an electric current is adapted to flow in the direction from the first electrode 12 toward the second electrode 18, so that a reference substance in the passage 10, e.g., oxygen in the ambient atmosphere is transferred into the cavity 8. Concurrently, unburned components of the measurement gas are introduced into the cavity 8 through the aperture 14 with a predetermined diffusion resistance, and stay in the vicinity of the first electrode 12. As a result, the unburned components in the cavity 8 are burned with the oxygen which is transferred from the side of the second electrode 18 to the side of the first electrode 12. A variation in electric current induced between the two electrodes 12, 18 is measured to detect the amounts of the unburned components, and consequently determine the condition of combustion (air-fuel ratio) that gives the detected specific amounts of the unburned components.

The planar solid electrolyte bodies 2, 4, 6 which are major or principal parts of the electrochemical cell, may be made of aluminum nitride, $SrCeO_3$, solid solution of bismuth oxide-oxide of rare earth element, $La_{1-x}Ca_xYO_{3-a}$, in place of previously indicated zirconia ceramics which is preferably used.

The electrochemical cell illustrated in FIG. 1 is manufactured in a known manner. For example, the electrodes 12, 18 and their leads 16, 20 are first printed, as by a screen-printing method, on green sheets of the first and third solid electrolyte bodies 2, 6. Then, the green sheets of the solid electrolyte bodies 2, 6 with the printed electrodes and leads, and a green sheet of the second solid electrolyte body 4, are superposed on each other so that the green sheet of the second solid electrolyte body 4 is sandwiched by the first and third solid electrolyte bodies 2, 6. Finally, the superposed green sheets are co-fired into the electrochemical cell of laminar structure.

In the case where the electrochemical device or cell is fabricated by using a co-firing method, it is preferred to co-fire the electrodes 12, 18 and their leads 16, 20. In this case, the electrodes and leads are printed, preferably using as major components thereof at least one element selected from the platinum group including platinum, palladium, rhodium, iridium, ruthenium and osmium. In this respect, it is desired to admix fine ceramic particles of zirconia, yttria, alumina, etc. with the materials of the electrodes and leads, for preventing flake-off and breakage thereof. With the addition of such ceramic particles, the adhesion of the electrodes and leads to the contacting layers is improved.

Referring to FIGS. 2 through 6, there are shown examples of modified forms of construction of the oxygen sensors.

Figure 2:
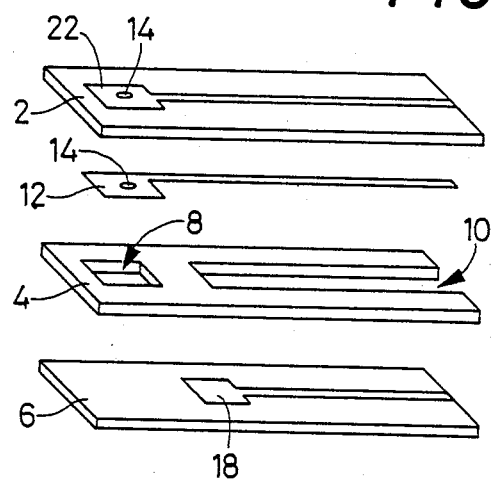
FIGS. 2-6 are exploded perpsective views, corresponding to FIG. 1, showing different modified forms of oxygen sensors similar to the oxygen sensor of FIG. 1.

A sensor shown in FIG. 2 is identical to the oxygen sensor of FIG. 1, with the exception that a third electrode 22 is provided as a pumping electrode on the outer surface of the first solid electrolyte body 2. In this modified oxygen sensor, the oxygen of the measurement gas in the cavity 8 is pumped out through the first solid electrolyte body 2 by applying a pumping voltage between the first and third electrodes 12, 22. Unlike the preceding embodiment, the instant embodiment uses the second electrode 18 only as a reference electrode. An electromotive force is measured between this reference electrode 18, and the first electrode 12 which also serves as a measuring electrode. Thus, the first electrode 12 serves commonly as the pumping and measuring electrodes. In this oxygen sensor, the first and third electrodes 12, 22 and the first solid electrolyte body 2 constitute a pumping cell, while the first and second electrodes 12, 18, and the third solid electrolyte body 6 constitute a sensing cell.

In the oxygen sensor of FIG. 2 wherein the electrodes 12, 22 of the pumping cell are disposed on opposite surfaces of the first solid electrolyte body 2, the impedance of the pumping cell is made lower, and consequently a large amount of oxygen can be pumped out of or into the cavity 8 in a shorter time, whereby the oxygen sensor is given a shorter response. This is an advantage of the modified form of FIG. 2.

It is noted here that the above oxygen sensor (electrochemical cell) also employs the useful arrangement according to the invention that the measurement-gas cavity 8 and the reference-gas passage 10 are spaced from each other in the direction of the surfaces of the planar solid electrolyte bodies, and located at substantially the same plane parallel to the solid electrolyte bodies (e.g. a portion of the measurement-gas cavity 8 and the reference-gas passage 10 are in the same plane parallel to a surface of said planar solid electrolyte body).

Figure 3:
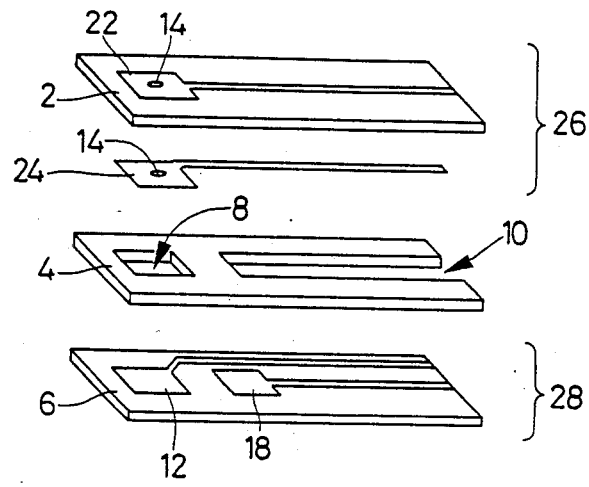

There is illustrated in FIG. 3 another modified oxygen sensor which takes an arrangement different from that of the preceding embodiment. More particularly described, the first electrode 12 is disposed on the surface of the third solid electrolyte body 6 on which the second electrode 18 is disposed. The first electrode 12 is spaced from the second electrode 18 such that the first electrode 12 is exposed to the cavity 8. While the second and third electrodes 18, 22 are disposed in the same locations as in the preceding embodiment, a fourth electrode 24 is additionally provided on the inner surface of the first solid electrolyte body 2 so that the electrode 24 is exposed to the cavity 8. Thus, the fourth electrode 24 is equivalent to the first electrode 12 of the preceding embodiment. The first electrode 12 of the instant embodiment of FIG. 3 functions as a measuring electrode contacting the measurement gas in the cavity 8, while the fourth electrode 24 functions as a pumping electrode.

As indicated above, the four electrodes 12, 18, 22 and 24 have independent functions. That is, the third and fourth electrodes 22 and 24 serve as a pair of pumping electrodes. Further, the second electrode 18 acts as a reference electrode while the first electrode 12 functions as a measuring electrode. Thus, in this modified arrangement, a pumping cell 26 constituted by the first solid electrolyte body 2 and the third and fourth electrodes 22, 24, is clearly delimited from a sensing cell 28 which is constituted by the third solid electrolyte body 6 and the first and second electrodes 12, 18.

It is further noted that the clearly separate arrangement of the pumping and sensing cells 26 and 28 contributes to reduction in leaking current from the pumping cell 26 toward the sensing cell 28, and thus offers an advantage of improved detecting accuracy of an electromotive force of the sensing cell 28. The detecting accuracy of the sensing cell 28 of this embodiment of FIG. 3 will be further enhanced by replacing the second solid electrolyte body by a ceramic layer having a high electric resistance, or by interposing such electrically resistant ceramic layer between the first and second solid electrolyte bodies 2 and 4, or between the second and third solid electrolyte bodies 4 and 6.

Figure 4:
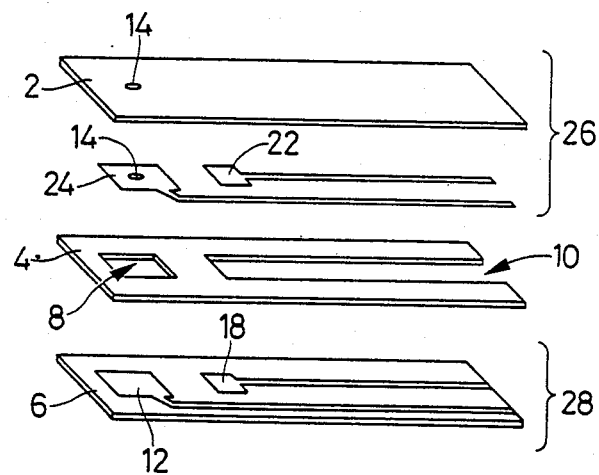

An oxygen sensor illustrated in FIG. 4 is an example in which the third electrode 22 is disposed on the inner surface of the first solid electrolyte body 2, unlike the electrode 22 of FIG. 3. Namely, the third electrode 22 and the fourth electrode 24 are disposed on the same side of the first solid electrolyte body 2, such that the third electrode 22 is exposed to the reference-substance space 10 formed in the second solid electrolyte body 4. When a pumping voltage is applied between the third and fourth electrodes 22 and 24, a current flows between the two electrodes 22, 24 through the first solid electrolyte body 2, whereby the oxygen in the cavity 8 is transferred into to or from the reference-gas passage 10 through the first solid electrolyte body 2. Thus, the oxygen in the cavity 8 is discharged or charged.

Since the upper pumping cell 26 (consisting of the first solid electrolyte body 2, and the third and fourth electrodes 22, 24) and the lower sensing cell 28 (consisting of the third solid electrolyte body 6, and the first and second electrodes 12, 18) are disposed symmetrically with each other in the instant oxygen sensor of FIG. 4, it is possible that the locations of the two cells are reversed, so that the upper cell is a pumping cell while the lower cell is a pumping cell.

Figure 5:
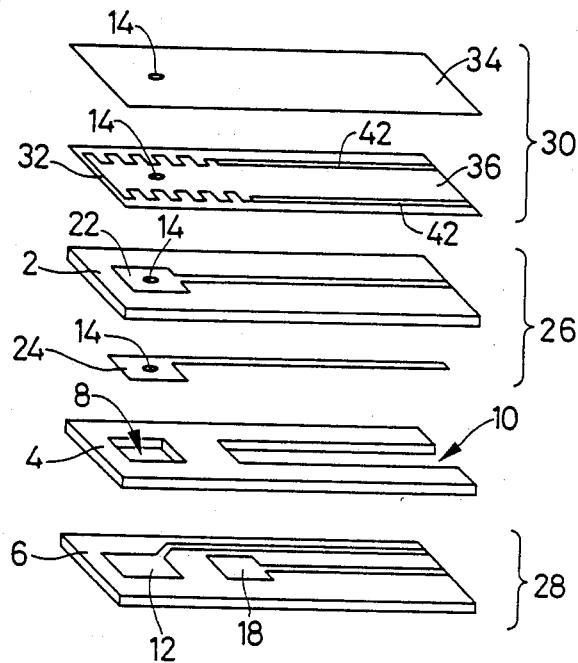

Referring to FIG. 5, there is shown an oxygen sensor which has the pumping and sensing cells similar to those of FIG. 3, but is provided with a ceramic heater 30. This heater 30 includes a heating element 32 sandwiched by electrically insulating layers 34 and 36, and is integrally laminated in contact with the first solid electrolyte body 2 of the pumping cell 26. The aperture 14 is formed so as to extend through the ceramic heater 30 as well as the pumping cell 26. The measurement gas, more precisely, a specific component (oxygen) of the measurement gas is introduced into the cavity 8 through the aperture 14 at a controlled rate of diffusion.

The oxygen sensor of FIG. 5 is advantageous thanks to the provision of the heater 30 which efficiently heats the solid electrolyte bodies 2 and 6 of the cells 26 and 28 to a desired temperature when the temperature of the measurement gas is low. As the sensor according to the invention is constructed to be comparatively thin, the cells 26, 28 are heated to the operating temperature in a reduced length of time.

The insulating layers 34, 36 which electrically insulate the heating element 32 and its leads 42, are generally layers of ceramics which preferably comprise alumina or spinel as a major component. However, the layers 34, 36 may be made of ceramics whose major component is borosilicate glass or mullite. It is desired that these insulating layers 34, 36 be as thin as possible as long as they demonstrate sufficient insulating property. Their thickness should generally be held not greater than 300 microns, preferably within a range of 10–200 microns. Further, it is preferred that the insulating layers 34, 36 are porous, in order to relax a thermal stress which may arise due to difference in coefficient of thermal expansion between the layers 34, 36 and the first solid electrolyte body 2. When the insulating layers 34, 36 are porous, the porous structure effectively prevents flake-off or peel-off troubles of the layers.

Figure 6:
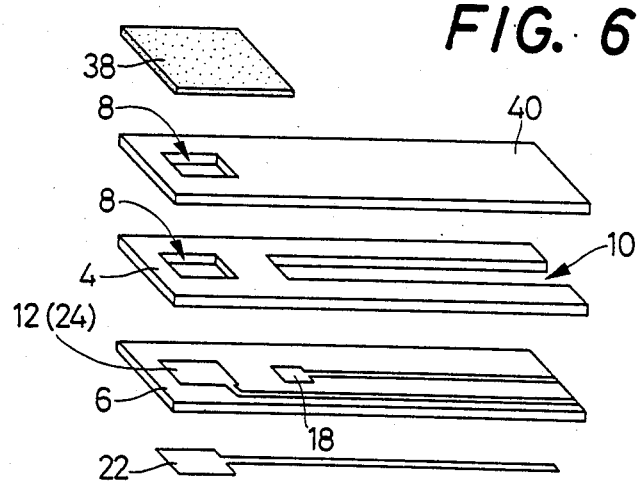

The present invention may be embodied as an oxygen sensor depicted in FIG. 6, wherein the first electrode 12 disposed on the inner surface of the third solid electrolyte body 6 serves also as the fourth electrode 24, while the third electrode 22 is disposed, in alignment with the first electrode, on the opposite outer surface of the third solid electrolyte body 6. In this arrangement, the oxygen in the cavity 8 is pumped out, or the oxygen and/or oxygen of oxides in the measurement gas is pumped into the cavity 8, through the third solid electrolyte body 6, according to the direction of flow of an electric current between the third and fourth electrodes 22 and 24.

Over the second solid electrolyte body 4, there are superposed a porous layer 38 which serves as diffusion-resistance means, and a covering layer 40 made of a suitable solid electrolyte material. The porosity of the porous layer 38 is selected to provide a predetermined diffusion resistance as previously indicated. These porous and covering layers 38, 40 are integrally laminated on the second solid electrolyte layer 4 in such a manner that the laminar assembly of the two layers 38, 40 covers the cutout and elongate slot formed in the second solid electrolyte body 4 for defining the cavity 8 and the passage 10. Stated in greater detail, the covering layer 40 partly defines the reference-gas passage 10, and has a rectangular cutout aligned with the cutout in the body 4 such that these two cutouts form the depth of the measurement-gas cavity 8. The cutout in the covering member 40 is closed by the porous layer 38.

In this oxygen sensor, too, the measurement-gas space (cavity 8) and the reference-gas· space (passage 10) are juxtaposed in spaced relation with each other along the surfaces of the solid electrolyte bodies, and located at substantially the same plane parallel to the plane of the solid electrolyte bodies, according to the principle of the invention. Therefore, the same operational effects as previously discussed are offered. While the cutout in the covering layer 40 increases the volume of the measurement-gas cavity 8 in this oxygen sensor, it is appreciated to utilize this covering layer 40 for increasing the volume of the reference-gas passage 10.

As is apparent from the foregoing description and from FIGS. 1-6, the electrochemical device constructed according to the invention is characterized in that the reference-gas space to which the first electrode is exposed, and the reference-gas space to which the second electrode is exposed, are disposed in mutually spaced-apart relation in substantially the same plane parallel to the surfaces of the planar solid electrolyte bodies of the electrochemical cell, (e.g., a portion of the reference-gas space and the measurement-gas space are in the same plane, said plane being parallel to a surface of said planar solid electrolyte body) whereby the cell is obtained with an appreciably reduced thickness, and smaller dimensions. Further, the reduced thickness of the cell assures a reduced temperature gradient in the direction of thickness of the cell, which contributes to the protection of the solid electrolyte bodies and consequently the cell (device) from damage or breakage due to thermal stress. In the case where the cell is heated, the reduced thickness also serves to minimize the time required for heating the cell to its operating temperature. The industrial significance of the above-illustrated electrochemical oxygen sensors is found to reside in these advantages.

Referring further to FIGS. 7 through 15, there will be described several forms of another preferred embodiment of the electrochemical device of present invention.

Figure 7:
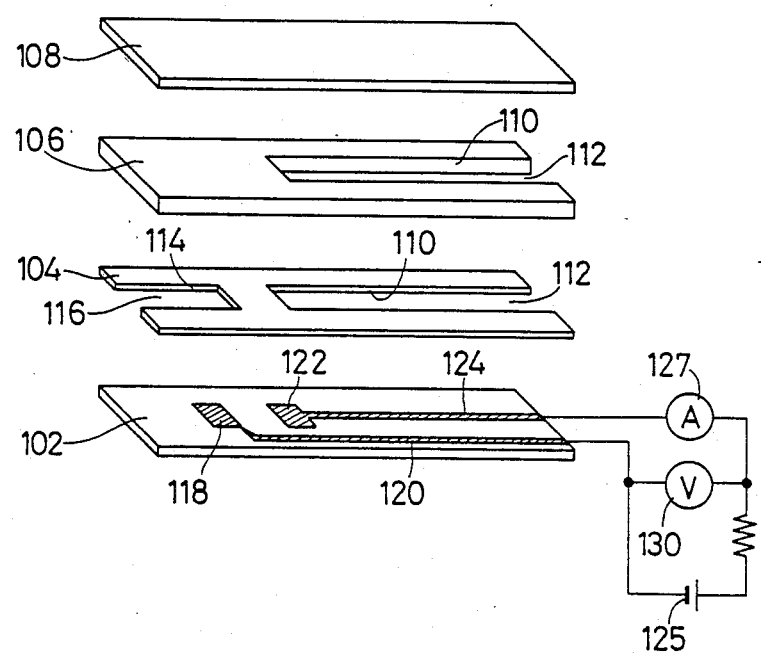
FIG. 7 is an exploded perspective view of a sensing element of another embodiment of an electrochemical device of the invention in the form of an oxygen sensor.

There is shown in the exploded perspective view of FIG. 7 a basic arrangement of a sensing element in one example of an oxygen sensor used in a modified embodiment of the invention. This oxygen sensor is of laminar structure comprising four layers or planar bodies of solid electrolyte 102, 104, 106 and 108 made of zirconia made of zirconia ceramics containing yttria. These solid electrolyte bodies are hereinafter referred to as cell substrate 102, spacer member 104, air-passage member 106 and covering member 108, respectively. The spacer member 104 and the air-passage member 106 have elongate recesses or slots 110 formed longitudinally thereof. These elongate slots 110 are covered by the cell substrate 102 and the covering member 108 which are disposed on the spacer and air-passage members 104 and 106, respectively, whereby an elongate air passage 112 for introducing a reference substance is formed in the sensing element. This air passage 112 corresponds to the passsage 10 in the preceding embodiment. The air passage 112 is open, at one end of the spacer member 104 and at one end of the air-passage member 106, to the ambient atmosphere. The spacer member 104 further has a longitudinal cut 114 in the other end portion thereof. This cutout 114 is covered by the cell substrate 102 and the air-passage member 106 on the opposite sides of the spacer member 104, whereby there is defined a thin flat space 116 with a very small depth as measured perpendicularly to the plane of the spacer member 104. The depth is selected so as to provide a predetermined diffusion resistance to molecules of a component of a measurement gas. The thin flat space 116 is open at the other end of the spacer member 104 remote from said one end at which the air passage 112 is open to the atmosphere. Thus, this thin flat space 116 corresponds to the cavity 8 of the preceding embodiment, and serves as the diffusion-resistance means as well as the measurement-gas space. The air passage 112 and the flat space 116 are formed in spaced-apart relation with each other at substantially the same plane parallel to the planar solid electrolyte body of the cell substrate 102.

The cell substrate 102 of the oxygen sensor has a first electrode 118 of porous structure made, for example, of platinum, on its inner surface, that is, on the surface not exposed to a measurement gas such as an exhaust gas. The first electrode 118 is located adjacent and exposed to the innermost portion of the flat space 116, and connected through its lead 120 to a suitable external device which will be described.

On the inner surface of the cell substrate 102, i.e., on the surface on which the first electrode 118 is disposed, there is provided a second electrode 122 of porous structure made of the same material as the first electrode. The second electrode 122 is located adjacent to the air passage 112 so that it is exposed to a reference substance, i.e., the ambient atmosphere in the air passage 112. The second electrode 122 is connected through its lead 124 to a suitable external device which will be described.

In the electrochemical sensor with the above-indicated construction, the first electrode 118 functions not only as a pumping electrode, but also as a measuring electrode for sensing the measurement gas introduced into the flat space 116. The second electrode 122 serves as another pumping electrode, and also as a reference electrode which is contacted with the ambient atmosphere (air) introduced as a reference substance into the air passage 112.

Stated more specifically referring to FIG. 7, by applying a suitable DC current between the first and second electrodes 118 and 122 through the leads 120 and 124, the oxygen sensor operates in the well known manner, to move the oxygen in the flat space 116 into the air passage 112 through the cell substrate 102, in the direction along the surface of the substrate 102. The amount of the oxygen to be moved toward the air passage 112 is varied in proportion to the amount of an electric current flowing between the electrodes 118, 122. In the meantime, the current flow and an electromotive force between the first and second electrodes 118, 122 exposed to the different atmospheres are measured by an ammeter 127 and a voltmeter 130, to determine the concentration of the oxygen of the measurement gas introduced in the flat space 116.

In the instant oxygen sensor, the oxygen component of the outside measurement gas is introduced into the flat space 116 through its opening in order to compensate for the amount of oxygen which is pumped out into the air passage 112 by a pumping operation with the first and second electrodes 118, 122. The introduced oxygen is directed to the first electrode 118 located at the innermost portion of the space 116. Since the flat space 116 is a gap of a very small depth or thickness, the rate of supply of the oxygen component into the flat space 116 is limited, whereby the oxygen partial pressure in the inner portion of the space 116 is made lower than that of the outside measurement gas. Consequently, the oxygen sensor is suitably used for measuring the oxygen concentration of a measurement gas whose oxygen partial pressure is relatively high, for example, as a sensor for controlling an engine which emanates an exhaust gas of lean air-fuel ratios whose oxygen partial pressure is higher than that of the stoichiometric air-fuel ratio.

However, the electrochemical device of the instant embodiment is also usable for determining the oxygen concentration of an equilibrated atmosphere such as an exhaust gas which is produced in combustion at the stoichiometric air-fuel ratio. In this case, an electromotive force between the first and second electrodes 118, 122 is measured, but an oxygen pumping function by application of a DC voltage between the electrodes is not attained.

Further, the instant basic arrangement of the electrochemical device is also usable as a rich-burn sensor, more particularly, a sensor for detecting unburned components of such an exhaust gas that is produced in combution at an air-fuel ratio in a fuel-rich range, which exhaust gas has an oxygen partial pressure lower than that of the stoichiometric air-fuel ratio and contains the unburned components in relatively large amounts. In this case, an electric current is adapted to flow in the direction from the first electrode 118 toward the second electrode 122, so that the oxygen in the ambient atmosphere in the air passage 112 is transferred into the flat space 116. Concurrently, unburned components of the measurement gas are introduced into the flat space 116 through its diffusion resistance, and stay in the vicinity of the first electrode 118 are burned with the oxygen which is transferred from the side of the second electrode 122 to the side of the first electrode 118. A variation in electric current induced between the two electrodes 118, 122 is measured to detect the amounts of the unburned components, and consequently determine the condition of combustion (air-fuel ratio) that gives the detected specific amounts of the unburned components.

The planar solid electrolyte bodies (102, 104, 106 and 108) may be made of ceramic materials other than zirconia ceramics, which are previously described in connection with the solid electrolyte bodies 2, 4 and 6 of the preceding embodiments.

The electrochemical device illustrated in FIG. 7 is manufactured in the same manner as previously described. For example, the electrodes 118, 122 and their leads 120, 124 are first printed, as by a screen-printing method, on a green sheet of the cell substrate 102. Then, the green sheet of the cell substrate 102 with the printed electrodes and leads, and planar green sheets of the spacer, air-passage and covering members 104, 106, 108 are superposed in stack on each other, and finally co-fired into the integral electrochemical cell of laminar structure.

In the fabrication of the laminar structure, it is appreciated that the cutout 114 in the spacer member 104 is loaded, prior to co-firing of the laminated assembly, with a suitable material which is burned out during a co-firing process, such as papers or thermosetting resin, so that such a filling permits formation of the cutout 116 having a predetermined diffusion resistance. Alternatively, the flat space 116 may be filled with a suitable porous ceramic layer with a predtermined diffusion resistance, to increase the mechanical strength of the cell around the formed flat space 116.

In the case where the electrochemical device or cell is fabricated by using a co-firing method, it is preferred to co-fire the electrodes 118, 122 and their leads 120, 124. In this case, the electrodes and leads are printed, preferably using as major components thereof at least one element selected from the the platinum group, as previously discussed in connection with the electrodes 12, 18, 22 and 24. In this respect, it is desired to admix fine ceramic particles of zirconia, yttria, alumina, etc. with the materials of the electrodes and leads, for the purposes indicated before in the description of the preceding embodiment.

Further modified forms of the oxygen sensors of this second embodiment are illustrated in FIGS. 8 through 15.

Figure 8:
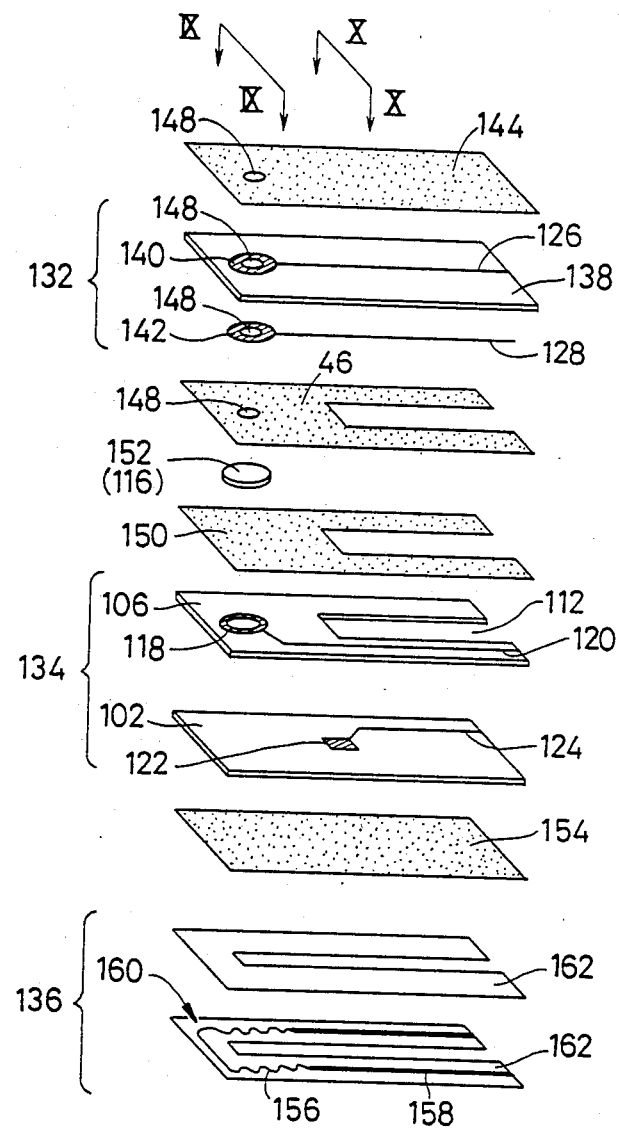
FIG. 8 is a view corresponding to FIG. 7, showing a modified form of an oxygen sensor similar to the sensor of FIG. 7.
Figure 9:
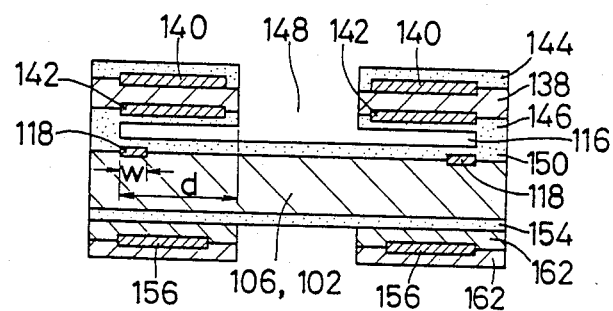
FIGS. 9 and 10 are schematic elevational views in cross section taken along lines 9—9 and 10—10 of FIG. 8, respectively.
Figure 10:
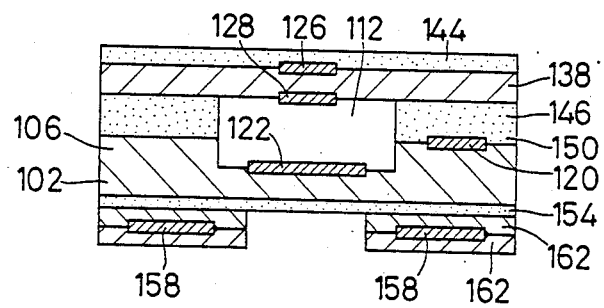

An electrochemical device showin in FIGS. 8–10 is a co-fired integral laminar assembly of an electrochemical pumping cell 132, an electrochemical sensing cell 134, and a ceramic heater 136. The electrochemical pumping cell 132 consists of a cell substrate 138 made of a solid electrolyte such as zirconia containing yttria, and an outer and an inner pumping electrode 140, 142 which are disposed in contact with the opposite surfaces of the cell substrate 138. Porous protective layers 144 and 146 are disposed on the opposite sides of the cell substrate 138 so as to cover the outer and inner pumping electrodes 140 and 142, respectively, and to thereby protect these electrodes against direct contact with a measurement gas.

The above indicated members, that is, the porous protective layer 144, outer pumping electrode 140, cell substrate 138, inner pumping electrode 142 and porous protective layer 146, have gas-inlet apertures 148 which are formed through the above members and have a diameter that provides a substantially negligible diffusion resistance. The outer and inner pumping electrodes 140, 142 of the electrochemical cell 132 are connected through their leads 126, 128 to an external DC power source. The oxygen of the measurement gas is moved from the inner pumping electrode 142 toward the outer pumping electrode 140 or vice versa through the solid electrolyte of the cell substrate 138, depending upon the direction of flow of an electric current between these electrodes.

The electrochemical cell 134 comprises the air-passage member 106 and cell substrate 102 of solid electrolyte which are superposed on each other. The first electrode 118, which is a ring with a small radial wall width, is disposed as a measuring electrode on the surface of the air-passage member 106. The second electrode 122 is disposed on the cell substrate 102 as a reference electrode which is exposed to the air passage 112 defined in the air-passage member 106. The surface of the air-passage member 106 on which the first electrode 118 is provided, is covered by a porous protective layer 150 which protects the first electrode 118 against direct contact with the measurement gas. An electromotive force is generated between the first and second electrodes 118, 122 due to difference in concentration of the oxygen component (oxygen partial pressure) of the different atmospheres adjacent to the first and second electrodes 118, 122, and the generated electromotive force is monitored through the leads 120, 124 by a suitable external device.

Between the porous protective layers 146 and 150 of the electrochemical pumping and sensing cells 132 and 134, there is interposed a suitable thermally-disappearing layer 152 with a small thickness, which disappears while the laminated assembly is co-fired. As a result, a circular flat space 116 with a small depth is formed between the two porous protective layers 146 and 150. The gas-inlet aperture 148 of the pumping cell 132 is open to an almost central portion of the flat space 116, as shown in FIG. 9, so that the outside measurement gas is introduced into the flat space through the aperture 148. If it is considered that the end portion of the aperture 148 occupies the central portion of the flat space 116, this space is regarded to take a substantially annular form. As shown in FIG. 9, the ring-shaped first electrode 118 of the sensing cell 134 is disposed in alignment with the radially outermost portion of the annular flat space 116 with the porous protective layer 150 sandwiched therebetween, whereby the first electrode 118 is contacted with the atmosphere in the flat space 116 through the porous protective layer 150. Similarly, the inner pumping electrode 142 of the pumping cell 132 is contacted with the atmosphere in the flat space 116 through the porous protective layer 146.

On the outer side of the cell substrate 102 of the sensing cell 134, i.e., on the surface opposite to the surface on which the second electrode 122 is disposed, there is provided a heating assembly 136 which is attached to the cell substrate 102 via a porous electrically insulating layer 154, such that the sensing cell 134 and the heating assembly 136 is an integral laminar structure. The heating assembly 136 includes a heater 160 consisting of a heating element 156 and leads 158 which are sandwiched by an upper and an lower ceramic layer 162, 162 having a high electric resistance. The heating element 156 is connected through the leads 158 to an external power source, so that the element 156 is energized to heat the solid electrolyte bodies (138, 106, 102) of the cells 132, 134, and their electrodes (140, 142, 118, 122) to their operating temperatures while the temperature of the measurement gas is relatively low. As the electrochemical oxygen sensor according to the invention is a laminar structure with a comparatively small thickness, the cells 132, 134 are heated to the operating temperature in a shorter period of time.

While the thin flat space 116 of the instant embodiment has a constant depth (thickness) over the entire area in its plane, from the opening to the periphery, this is not always a requirement. Rather, it is preferred that the flat space 116 is stepped or tapered for increasing depth at its portion adjacent to the opening to the aperture 148. This modification is effective for minimizing an adverse effect of pressure pulsation of an exhaust gas from an internal combustion engine, for example, and for improving a response of the electrochemical device. In this connection, the depth of the flat space 116 is preferably held within a range of 1–100 microns, approximately.

While the ring-shaped first electrode 118 is disposed substantially in alignment with the radially outermost portion of the annular flat space 116 as illustrated in FIG. 9 and previously stated, the radial wall width "w" of the ring 118 is preferably within a range from 0.1d to 0.5d, where "d" represents a distance between the outer and inner peripheries of the annulus of the annular flat space 116 whose inner periphery is concentric with the diameter of the gas-inlet aperture 148. Described differently, the ring-shaped first electrode 118 is located relative to the annular space 116 such that the inner periphery of the electrode 118 is spaced from the inner periphery of the annulus of the annular space 116 by a distance equal to 0.5–0.9d. This arrangement contributes to minimization of a gradient of concentration of the measurement component which is diffused radially of the annular flat space 116 toward the outer periphery, thereby permits the sensing cell 134 to obtain a sharp "λ" curve, that is, enhanced detecting accuracy of the cell.

The inner pumping electrode 142 of the pumping cell 132 exposed to the atmosphere in the annular flat space 116 is preferably so disposed that its outer periphery is substantially aligned with the outer periphery of the annulus of the annular space 116. Further, it is preferred to dimension the inner pumping electrode 142 such that space above said electrode 142 is not greater than 70% of the total space of the annular space 116. This arrangement of the inner pumping electrode 142 relative to the annular space 116 effectively eliminates an adverse effect that would be otherwise caused due to pressure variation (pulsation) of the measurement gas introduced through the aperture 148 into the annular space 116.

The oxygen sensor (electrochemical device) which has been described also enjoys the previously indicated advantages which accrue from the unique arrangement according to the invention wherein the flat space 116 and the air passage 112 are disposed in spaced-apart relation with each other at substantially the same plane parallel to the plane of the laminated bodies of solid electrolyte (138, 106, 102), that is, the space 116 and the passage 112 are juxtaposed at substantially the same level parallel to the plane of the planar laminar structure of the oxygen sensor.

Figure 11:
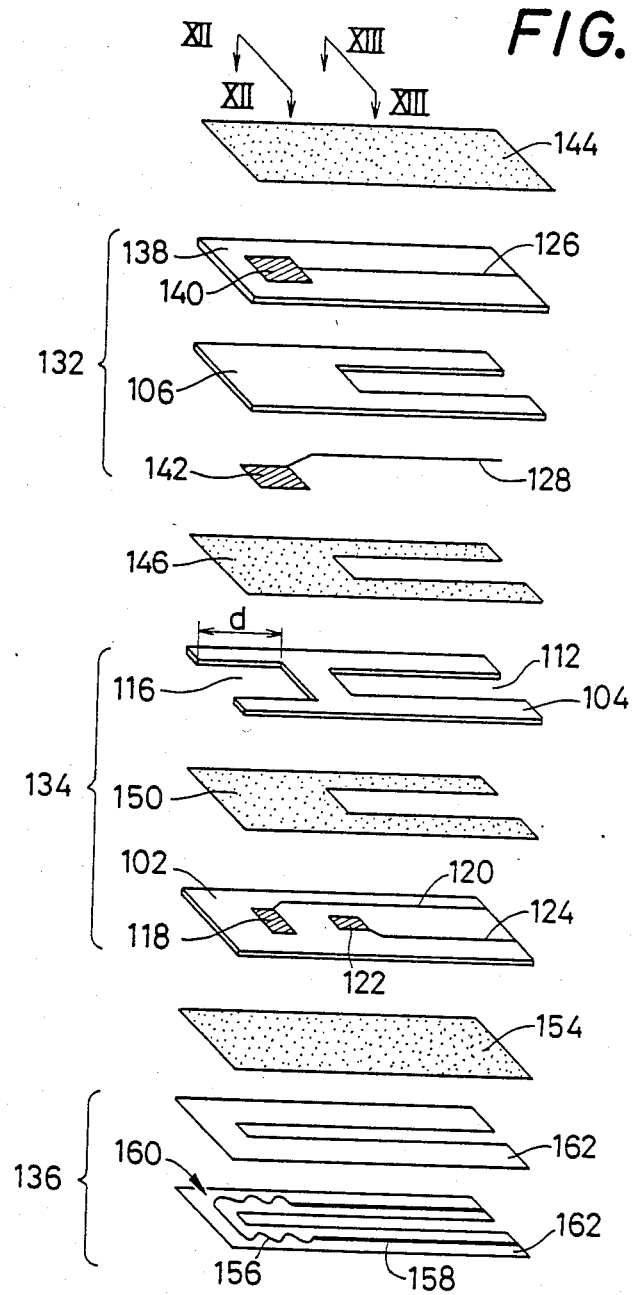
FIG. 11 is a view corresponding to FIG. 7, showing another modified oxygen sensor similar to the sensors of FIGS. 7 and 8.
Figure 12:
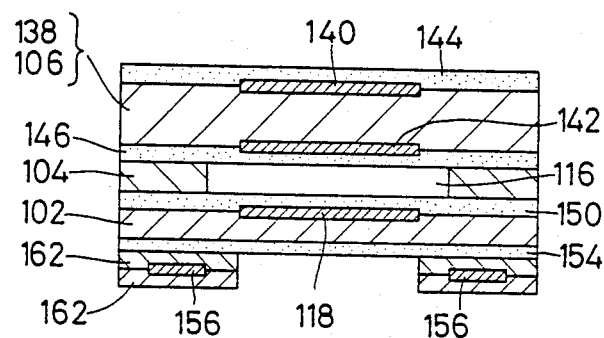
FIGS. 12 and 13 are schematic elevational views in cross section taken along lines 12—12 and 13—13 of FIG. 11.
Figure 13:
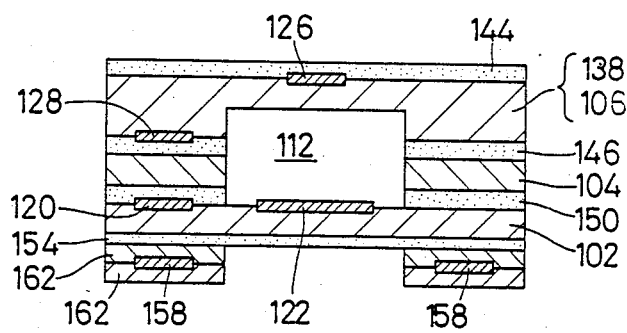

A further modified oxygen sensor is depicted in FIGS. 11–13. Unlike the preceding arrangement (shown in FIGS. 8–10), the oxygen sensor of this arrangement has a thin flat space 116 which is similar to the space 116 provided in the sensor of FIG. 7. That is, the flat space 116 is open to the outside at one longitudinal end of the sensor, so that the measurement component in the outside measurement gas is introduced through the opening of the flat space 116 and diffused into the inner portion of the space, with a diffusion resistance to molecules of the component. This diffusion resistance is created by a very small depth (thickness) of the flat space 116. The diffused component staying in the inner portion of the flat space 116 is contacted, through the porous protective layer 150, with the first electrode 118 which, in this modification, is an elongate strip disposed across the width of the flat space 116.

The inner pumping electrode 142 of the electrochemical pumping cell 132 is also exposed to the atmosphere in the flat space 116, through the porous protective layer 146. This inner pumping electrode 142 is located substantially in alignment with the inner portion of the flat space 116, and dimensioned so that space above said electrode 142 is not greater than 70% of the total space of the flat space 116. Similarly, first electrode 118 disposed across the width of the flat space 116 is located or around at the innermost portion of the space 116, and dimensioned so that its width is within a range of 0.1–0.5d where "d" represents a length of the space 116 longitudinally of the cell 134. In other words, the outer edge of the first electrode 118 on the side of the opening of the space 116 is spaced, by a distance of 0.5–0.9d, from the open end of the flat space 116.

In the above oxygen sensor, the pumping cell 132 is clearly delimited from the sensing cell 134 as in the preceding arrangement of FIGS. 8–10. The sensing cell 134 is effectively protected from influence of a leaking current from the pumping cell 132, whereby the accuracy of detection of an electromotive force by the sensing cell 134 is improved. More particularly, the porous protective layers 146 and 150, and/or the spacer member 104 should be made of a ceramic material which has a high electric resistance.

Figure 14:
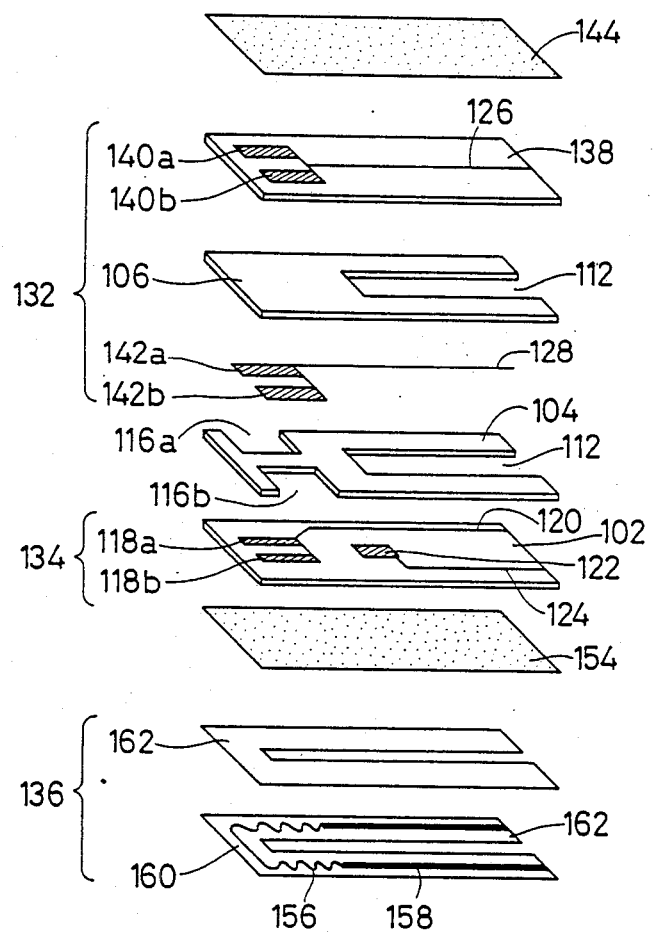
FIGS. 14 and 15 are views illustrating further modified forms of oxygen sensors similar to those of FIGS. 8 and 11.

There is shown in FIG. 14 another modified form of the oxygen sensor, which is similar to the preceding two sensors, in that the electrochemical pumping and sensing cells 132, 134 and the heating assembly 136 constitute a laminar structure of the sensor. However, the instant arrangement is different from the preceding two arrangements and characterized in that a thin flat space having a small depth (across the thickness of the air-passage member 104) to provide a predetermined diffusion resistance is divided into two flat spaces 116a, 116b. Described in greater detail, the two flat spaces 116a, 116b are formed in the air-passage member 104 symmetrically with each other such that the flat spaces are open to the outside at the opposite longitudinal side edges thereof. Corresponding two first electrodes 118a, 118b are disposed adjacent to the transversely innermost portions of these two flat spaces 116a, 116b.

In this modified arrangement, two inner pumping electrodes 142a, 142b of the pumping cell 132 are disposed so as to correspond to the two flat spaces 116a, 116b. Similarly, two outer pumping electrodes 140a, 14b are provided corresponding to the two inner pumping electrodes 142a, 142b.

Obviously, the two thin flat spaces 116a, 116b formed with a small depth to provide a predetermined diffusion reistance in the instant oxygen sensor, are juxtaposed in spaced-apart relation with the air passage 112 in substantially the same plane parallel to the plane of the solid electrolyte body (cell substrate 102). This co-planar arrangement of the flat spaces 116a, 116b and the air passage 112 according to the invention is effective for reducing the total thickness of the oxygen sensor.

Figure 15:
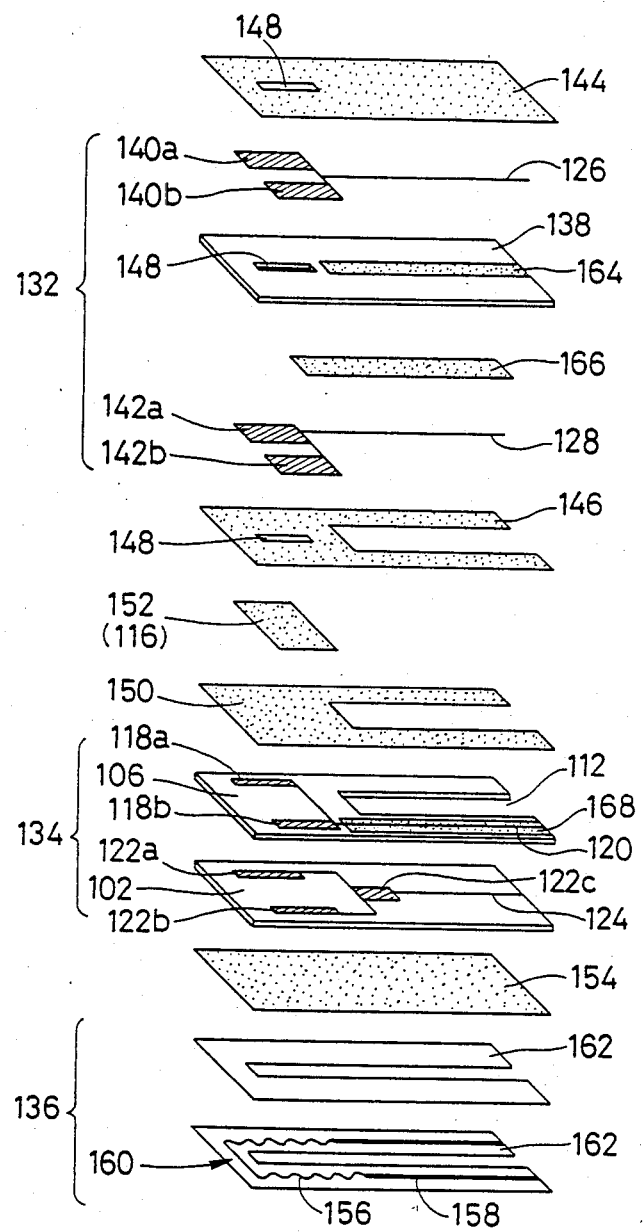

An oxygen sensor shown in FIG. 15 also according to the invention is a modification of the oxygen sensor of FIG. 8. This modified sensor is characterized by the gas-inlet aperture 148 formed through the pumping cell 132. That is, the aperture 148 of FIG. 15 has an elongate rectangular shape, contrary to the aperture 148 of the sensor of FIG. 8. The pumping cell 132 has a pair of outer pumping electrodes 140a, 140b, and a pair of inner pumping electrodes 142a, 142b, such that the rectangular aperture 148 is located between the two electrodes of each pair. Reference numerals 164 and 166 designate porous insulating layers for protecting the leads of the pumping electrodes.

The disappearing layer 152 to form the flat space 116 with a predetermined diffusion resistance has a rectangular shape extending transversely of the cell 132, and is disposed so that the rectangular gas-inlet aperture 148 is aligned with its central portion along the length. The disappearing layer 152 disappears while the laminar structure of the oxygen sensor is co-fired, whereby a flat space 116 with a predetermined depth is formed between the porous protective layers 146 and 150, in communication with the rectangular aperture 148.

Although the gas-inlet aperture 148 of the present oxygen sensor is provided only in the pumping cell 132, it is possible that the aperture 148 is formed through the sensing cell 134, or through both of the pumping and sensing cells 132, 134. At any rate, the aperture 148 should be formed in communication with the flat space 116.

As indicated above, the rectangular thin flat space 116 is formed so as to extend transversely of the cells 132, 134, and the gas-inlet aperture 148 is open to the flat space 116 at its central portion. A pair of first electrodes 118a, 118b of the sensing cell 134 are disposed on the air-passage member 106 so that the electrodes 118a, 118b are aligned with the opposite end portions of the rectangular flat space 116. The lead 120 of the first electrodes 118a, 118b is electrically insulated from the air-passage member 106 by a porous insulating layer 168.

Further, two electrodes 122a, 122b are disposed on the cell substrate 102 so that they are opposite to the two first electrodes 118a, 118b with the air-passage member 106 therebetween. Further, an electrode 122c is disposed on the cell substrate 102 so that it is exposed to the air passage 112. These three electrodes 122a, 122b and 122c are connected to each other and constitute the second electrode 122 of the sensing cell 134. In this arrangement wherein the second electrode 122 comprises the two electrodes aligned with the first electrodes 118a, 118b, the impedance of the sensing cell 134 is made lower, and its detecting performance is improved.

In the oxygen sensor of FIG. 15, too, the rectangular flat space 116 having a predetermined diffusion resistance, and the air passage 112 are spaced from each other at substantially the same plane parallel to the plane of the cells, i.e., parallel to the surfaces of the planar cell substrate 102 of solid electrolyte. Thus, the oxygen sensor enjoys the previously discussed benefits thanks to this co-planar arrangement of the flat space 116 and the air passage 112.

As in the oxygen sensors of the preceding embodiment of FIGS. 1–6, the electrochemical sensors of FIGS. 7–15 are also characterized in that the thin flat space 116 serving as diffusion-resistance means to which the first electrode is exposed, and the reference-gas passage or space 112 to which the second electrode is exposed, are disposed in mutually spaced-apart relation in substantially the same plane parallel to the surfaces of the planar solid electrolyte bodies of the electrochemical cell, whereby the cell is obtained with an appreciably reduced thickness, and smaller dimensions. This reduced thickness provides other benefits described in connection with the first embodiment of FIGS. 1–6.

Referring further to FIGS. 16–20, some different oxygen sensors of a further modified embodiment of the inventon will be described.

Figure 16:
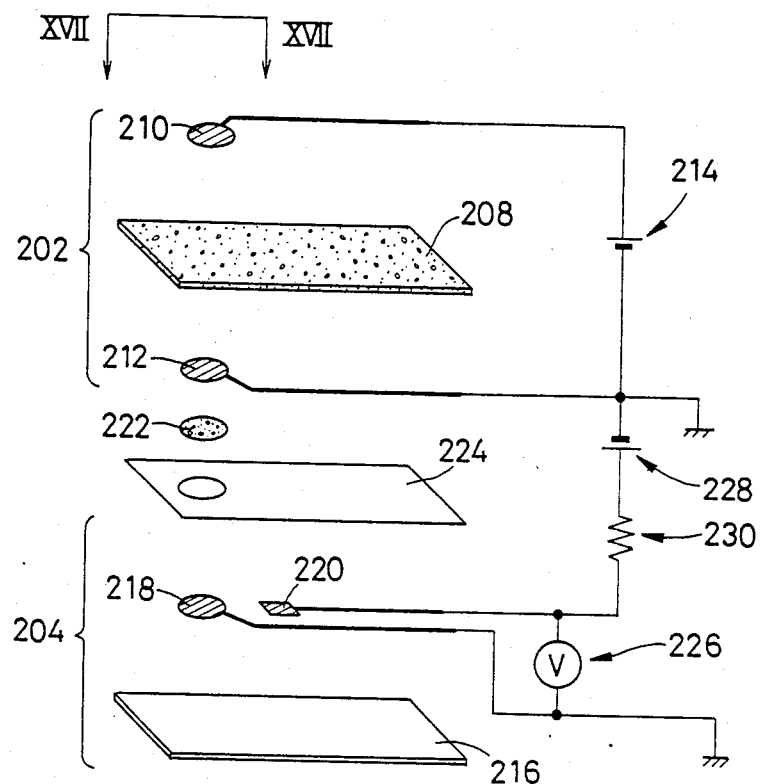
FIG. 16 is an exploded perspective view of a sensing element in the form of an oxygen sensor of a further embodiment of an electrochemical device of the invention.
Figure 16:
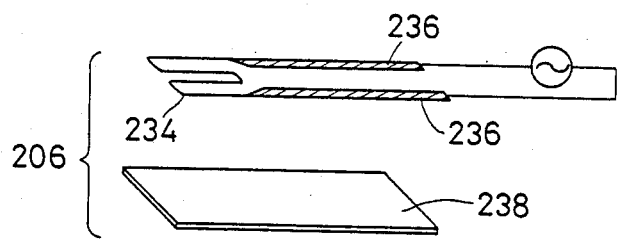
Figure 17:
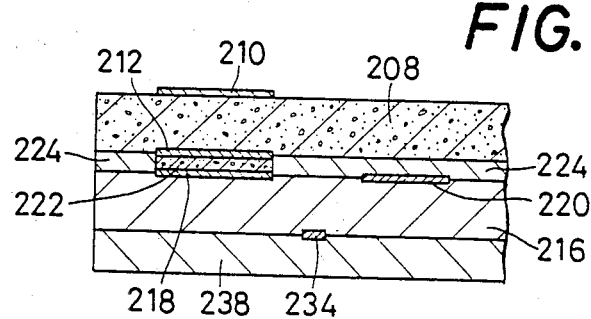
FIG. 17 is a schematic elevational view in cross section taken along line 17—17 of FIG. 16.

In the exploded perspective view of FIG. 16, there is illustrated a basic arrangement of an oxygen concentration sensing element associated with this third embodiment of the electrochemical device of the invention. FIG. 17 shows the sensing element in longitudinal cross section, in enlargement in the direction of thickness of the sensing element. This oxygen concentration sensing element (oxygen sensor) is one of so-called "lean-burn sensors", which is an integral co-fired laminar structure comprising an oxygen pumping cell 202, an oxygen concentration sensing cell 204, and a heater 206, with the sensing cell 204 sandwiched by the pumping cell 202 and the heater 206.

The oxygen pumping cell 202, which is one component of the sensing element, includes a planar porous body 208 of oxygen-ion conductive solid electrolyte (first solid electrolyte body 208) which is made, for example, of zirconia ceramics containing yttria. The planar porous solid electrolyte body 208 has a porous outer pumping electrode 210 on one of its opposite surfaces, i.e., on the surface exposed to a measurement gas such as an exhaust gas. The outer pumping electrode 210 is made, for example, of platinum-zirconia. On the other surface (inner surface) of the porous solid electrolyte body 208, there is disposed an inner pumping electrode 212 which is aligned with the outer pumping electrode 210. This inner pumping electrode 212 is made of the same material as the outer pumping electrode 210, that is, made of porous platinum-zirconia. The pumping electrodes 210, 212 are connected to an external power source 214 through their leads, so that a predetermined amount 'of electric current flows between the two electrodes 210, 212.

The porous solid electrolyte body 208 functions as a diffusion-resistance layer through which a selected component, for example, oxygen, of the measurement gas is diffused from one surface thereof to the other surface. The pores in the solid electrolyte body 208 provide a predetermined diffusion resistance to molecules of the selected component. Thus, the solid electrolyte body 208 corresponds to the porous ceramic layer 38 of FIG. 6 of the first embodiment. In this electrochemical pumping cell 202 consisting of the porous solid electrolyte body 208 and the pair of pumping electrodes 210, 212 on the outer and inner surfaces of the body 208, the oxygen in the measurement gas is diffused to the side of the inner pumping electrode 212 through the porous structure of the solid electrolyte body 208, and the oxygen around the inner pumping electrode 212 is pumped out toward the outer pumping electrode 210 and discharged into the outside measurement gas by means of a well known pumping action by applying a suitable voltage between the two electrodes 210, 212. The amount of oxygen to be discharged is varied in proportion to the amount of an electric current flowing through the electrodes 210, 212.

Unlike the oxygen pumping cell 202, the oxygen sensing cell 204 uses a planar gastight body 216 of solid electrolyte made of zirconia ceramics containing yttria, or the like. On the inner surface of the gastight solid electrolyte body 216, i.e., on the surface on the side of the pumping cell 202, there are disposed a porous measuring electrode 218 and a porous reference electrode 220, such that the measuring electrode 218 is aligned with the inner pumping electrode 212 and exposed to the atmosphere existing in the vicinity of the inner pumping electrode 212, and such that the measuring and reference electrodes 218 and 220 are juxtaposed in spaced-apart relation with each other. As described later, the reference electrode 220 is protected by gastight ceramic layers from exposure to the measurement gas. Thus, the second solid electrolyte body 216 and the measuring and reference electrodes 218, 220 constitute an electrochemical cell in the form of the oxygen concentration sensing cell 204.

Between the measuring electrode 218 of the sensing cell 204 and the inner pumping electrode 212 of the pumping cell 202, there is interposed a thin porous ceramic layer 222 made of alumina or zirconia, or the like. Through this porous ceramic layer 222, the electrodes 212 and 218 are concurrently exposed to the same atmosphere. In other words, the measuring electrode 218 is exposed to the atmosphere which is controlled by the previously indicated pumping action, and which exists around the inner pumping electrode 212. A gastight ceramic layer 224 of zirconia or like material having a high electric resistance is interposed between the pumping cell 202 and the gastight solid electrolyte body 216, so as to cooperate with the solid electrolyte body 216 to sandwich the reference electrode 220 which is spaced from the measuring electrode 218. In other words, the reference electrode 220 is embedded or encapsulated by the two gastight ceramic layers 224, 216, and thereby protected from exposure to the measurement gas.

These measuring and reference electrodes 218, 220 are connected through their leads to a suitable external measuring device (potentiometer 226) for measuring an electric potential between the two electrodes. Stated in detail, the oxygen concentration sensing cell 204 is adapted to measure an electromotive force based on a difference in concentration of oxygen between the reference electrode 220 which is held at a high potential of oxygen concentration by a separate pumping action, and the measuring electrode 218 which is contacted with the atmosphere which exists around the inner pumping electrode 212 and contains the controlled amount of oxygen from the outside measurement gas. Reference numerals 228 and 230 in FIG. 16 indicate a power source and a resistor incorporated in the electromotive force measuring circuit. With a voltage applied with the power source 228 between the inner pumping electrode 212 (and measuring electrode 218) and the reference electrode 220, the oxygen component is transferred from the inner pumping electrode 212 (and measuring electrode 218) to the reference electrode 220 which has the porous structure. With this separate pumping action, the oxygen component is accommodated as a reference gas in the porous structure of the reference electrode 220. That is, the reference electrode 220 is contacted with the reference gas existing in its pores. Thus, the pores in the reference electrode 220 serves as a reference-gas space.

The heater 206 is disposed in contact with the outer surface of the oxygen concentration sensing cell 204, i.e., on the surface remote from the oxygen pumping cell 202 and opposite to the surface on which the electrodes 218, 220 are disposed. The heater 206 consists of an integral assembly of a ceramic layer 238 made of zirconia or the like, and a heating element 234 and its leads 236, which are formed on the ceramic layer 238. The heater 206 is attached to the outer side of the sensing cell 204, so that the heating element 234 is aligned with the measuring electrode 218 which are aligned with the outer and inner pumping electrodes 210, 212. Heat is generated from the heating element 234 upon energization thereof with DC power supplied through the leads 236 from an external power source.

In the electrochemical device (sensing element) of FIGS. 16 and 17 wherein the heater 206 is not directly contact with the pumping cell 202, but positioned in close proximity with the oxygen concentration sensing cell 204, the diffusion of the oxygen component through the pumping cell 202 is not affected by the pattern of the heating element 234. Further, since the heating element 234 is formed so as to cover the entire area of the pumping electrodes 210, 212 and their vicinities, the pumping electrodes 210, 212 are heated uniformly over the entire surfaces with even heat distribution.

While the oxygen pumping cell 202 is heated by the heater 206 via the oxygen concentration sensing cell 204, the reference electrode 220 is disposed so as not to overlap the measuring electrode 218, that is, the reference electrode 220 is spaced from the measuring electrode 218 so that the reference electrode 220 will not intercept the heat from the heater 206 toward the pumping cell 202. Accordingly, the pumping cell 202, more particularly, their electrodes 210, 212 are more effectively heated by the heater 206. In other words, the spaced-apart arrangement of the measuring and reference electrodes 218, 220 of the sensing cell 204 allows increased efficiency of heat transfer from the heater 206 to the pumping cell 202, thereby improving the pumping ability of the pumping cell and prolonging its service life.

In the case where a suitable reference-gas space is formed adjacent to the reference electrode 220, the spaced-apart positioning of the reference electrode 220 relative to the measuring electrode 218 is particularly effective, because such a space is not formed on the heat transfer path from the heating element 234 toward the pumping electrodes 210, 212.

A further advantage of the present electrochemical device lies in the fine porous structure of the solid electrolyte body 208 of the pumping cell 202, which porous structure functions as a diffusion-resistance layer through which the oxygen in the outside measurement gas is diffused toward the inner pumping electrode 212. This arrangement for introducing the oxygen into the interior of the device is less liable to suffer a trouble of timewise variation in diffusion resistance due to accumulation of soots or other substance on the cell, as compared with a conventional arrangement wherein a pin hole or leak aperture is formed as a diffusion hole for communication between the outside atmosphere (measurement gas), and a cavity formed within the device.

In the electrochemical device with the above-described construction, the oxygen partial pressure (concentration) of the atmosphere with which the measuring electrode 218 of the sensing cell 204 contacts, is controled by way of a pumping action of the pumping cell 202 and by means of a diffusion resistance of the porous solid electrolyte body 208 serving as a diffusion-resistance layer, so that the oxygen partial pressure in question is made lower than that of the outside measurement gas. Consequently, the instant electrochemical oxygen sensor is suitably used as a lean-burn sensor for controlling an engine which emanates an exhaust gas of lean air-fuel ratio whose oxygen partial pressure is higher than that of the stoichiometric air-fuel ratio.

The planar solid electrolyte bodies 208, 216 of the pumping and sensing cells 202, 204 may be made of other ceramic materials than zirconia ceramics, as previously described in connection with the solid electrolyte bodies 2, 4 and 6 of the first embodiment. As stated before, the solid electrolyte body 208 of the pumping cell 202 should be porous because it serves as a diffusion-resistance layer having a predetermined diffusion resistance to molecules of a selected component of a measurement gas. The porosity of the porous structure of the solid electrolyte body 208 is suitably selected depending upon the required level of diffusion resistance, and upon a specific method of fabrication of the body 208. If the body 208 is fabricated in a sintering process, for example, the porosity is preferably held within a range of approx. 2-30% as measured according to a mercury porosimetric method (measured by Mercury Porosimeter Type 70H made by Carlo Erba, Italy). If a plasma spraying process is used to manufacture the body 208, the preferred porosity range is 0.5-10% as measured with the same method.

The ceramic layer 222 interposed between the inner pumping electrode 212 of the pumping cell 202 and the measuring electrode 218 of the sensing cell 204, should be a porous layer, preferably a thin porous layer, since the electrodes 212 and 218 are exposed to the same atmosphere through this ceramic layer. The gastight ceramic layer 224 which cooperates with the solid electrolyte body 216 to gas-tightly enclose the reference electrode 220, may be made of various known ceramic materials such as zirconia, alumina, mullite, spinel, titania, barium titanate and calcium zirconate. Among these ceramics, zirconia is most preferably used as a major component of the gastight ceramic layer 224.

The ceramic layer 238 supporting the heating element 234 and leads 236 of the heater 206 is preferably a gastight layer made of ceramic materials indicated above for the gastight ceramic layer 224. The heating element 234 and leads 236 are layers which are made of a mixture of at least one element selected from the platinum group consisting of platinum, palladium, rhodium, iridium, ruthenium and osmium, and ceramics such as zirconia, yttria and alumina. Accordingly, the adhesion between the heating element and leads 234, 236 of the heater 206, and the surrounding ceramic layers 216, 238 is appreciably improved. In preparing a mixture material for forming the heating element and leads by firing, it is advantageous to admix fine particles of the above indicated ceramic material with a mass of powder of the above indicated platinum group.

For improving the adhesion of the electrodes 210, 212, 218 and 220 of the cells 202, 204, and their leads, it is also preferred to use a mixture of the above indicated platinum group element(s) and ceramics which are suitably used for the heater components (234, 236), as indicated before.

For manufacturing the electrochemical oxygen sensor of laminar structure consisting of the pumping cell 202, sensing cell 204 and heater 206 which have been described, the same methods as previously indicated are employed. For example, the electrodes and their leads are first printed, as by a screen-printing method, on green sheets of the solid electrolyte bodies 208, 216. In the meantime, the porous ceramic layer 222 and gastight ceramic layer 224 are formed by printing on one of the pumping and sensing cells 202, 204, while the heating element and leads 234, 236, and the ceramic layer 238 are printed in order on the outer surface of the solid electrolyte body 216 of the sensing cell 204. The prepared assembly of the pumping cell 202, and the prepared assembly of the sensing cell 204 with the heater 206, are assembled in stack into a laminar structure and co-fired into the intended electrochemical sensing element. For improved strength of the sensing element, however, it is possible to first co-fire the laminated assembly without the porous solid electrolyte body 208, and then form the porous solid electrolyte body 208 in a plasma spraying process.

Figure 19:
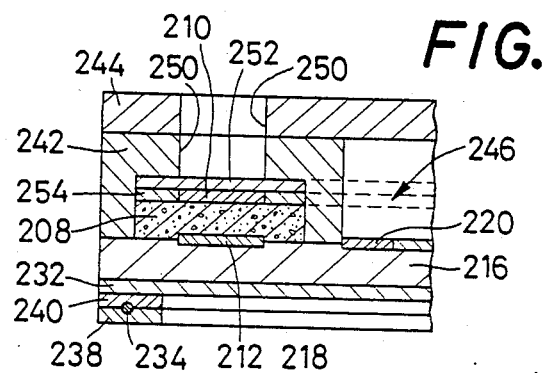
FIG. 19 is a cross sectional view of the oxygen sensor of FIG. 18, taken along line 19—19 of FIG. 18.
Figure 18:
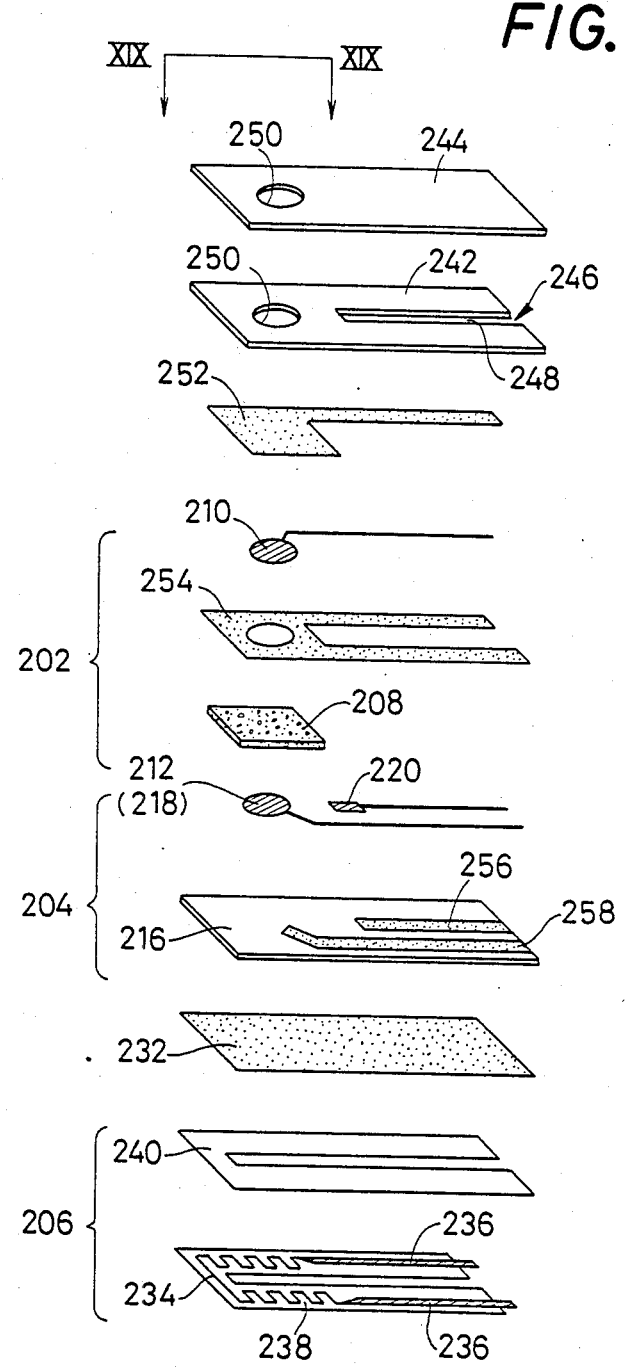
FIG. 18 is a view corresponding to FIG. 16, showing a modified form of an oxygen sensor similar to the sensor of FIG. 16.

An example of modified form of construction of this third embodiment of the invention is illustrated in FIGS. 18 and 19.

Unlike the preceding arrangement, an electrochemical device shown in FIGS. 18 and 19 uses a single electrode member which commonly serves as the inner pumping electrode 212 of the pumping cell 202, and as the measuring electrode 218. Thus, the instant sensor is simplified in construction, and comparatively economical to manufacture.

The gastight solid electrolyte body 216 of the sensing cell 204 cooperates with a spacer member 242 and a covering member 244 both made of a gastight ceramic material, to define a reference-gas passage 246 which is open at one end to the ambient atmosphere. The reference electrode 220 is located such that it is exposed to the atmosphere introduced in the reference-gas passage 246. This is an outstanding feature of this modified construction. Described in greater detail, the spacer member 242 has an elongate cutout (slot) 248, and is covered on its opposite sides by the upper covering member 244 and the lower pumping and sensing cells 202, 204, so that the reference-gas passage 246 is formed as shown in FIG. 19. This reference-gas passage is in communication with the ambient atmosphere through the opening at one end of the cutout 248 in the spacer member 242. Contrary to the preceding device, the instant electrochemical device uses the ambient atmosphere as a reference atmosphere to which the reference electrode 220 is exposed. Due to a difference in concentration of oxygen between the ambient atmosphere in the reference-gas passage 246, and the controlled atmosphere of the measurement gas in the vicinity of the measuring electrode 218, an electromotive force is generated between the measuring and reference electrodes 218 and 220, and measured in the known manner.

A gas-inlet aperture 250 is formed through portions of the spacer and covering members 242, 244 in alignment with the outer pumping electrode 210. Between the spacer member 242 and the outer pumping electrode 210, there is interposed a porous electrode protective layer 252 made of alumina. The outside measurement gas is introduced to the outer pumping electrode 210 through the gas-inlet aperture 250 and through the porous electrode protective layer 252, in a direction normal to the plane of the pumping electrode 210. Stated the other way, the gas-inlet aperture 250 in the gastight ceramic layers 242, 244 over the outer pumping electrode 210 functions as a gas-inlet layer to control the direction of entry of the outside measurement gas, so that the gas is directed perpendicularly to the surface of the diffusion-resistance layer of the porous solid electrolyte body 208, that is, to prevent the measurement gas from reaching the outer pumping electrode 210 laterally of its surface. In this arrangement, the measurement gas whose flow is controlled by the aperture 250 is diffused through the electrode 210 and the porous solid electrolyte body 208 in the direction normal to their surfaces, whereby the amount of gas to be introduced can be suitably controlled.

In this connection, it is noted that the porous structure of the solid electrolyte body 208 serves as diffusion-resistance means having a predetermined resistance to molecules of oxygen in the measurement gas, and further functions as a measurement-gas space to which the inner pumping electrode 212 and the measuring electrode 218 are exposed. It is further noted that this measurement-gas space (porous structure 208) and the reference-gas passage 246 are juxtaposed in spaced-apart relation in substantially the same plane. Therefore, the thickness of the oxygen sensor is reduced, as in the previous embodiments.

In the instant modified sensor, the heating element 234 and leads 236 of the heater 206 are sandwiched by gastight ceramic layers 238 and 240 made of zirconia or the like having a high electric resistance. The heater 206 is attached to the outer surface of the sensing cell 204 via an insulating layer 232 made of porous alumina or like material, and connected to an external DC power source. Reference numerals 254, 256, 258 indicate insulating layers of porous alumina or the like, which electrically insulate the leads for the electrodes, like the electrode protective layer 252 for insulation of the outer pumping electrode 210.

In this illustrated arrangement wherein the reference electrode 220 is exposed to the reference-gas passage 246, the spaced-apart positioning of the reference electrode 220 relative to the measuring electrode 218 prevents the reference-gas passage 246 from being interposed between the pumping electrodes 210, 212 and the heating element 234 of the heater 206 and thereby intercepting the heat from the heater. Thus, the effect of the spaced-apart arrangement of the electrodes 218, 220 is more prominent than in the preceding arrangement.

Figure 20:
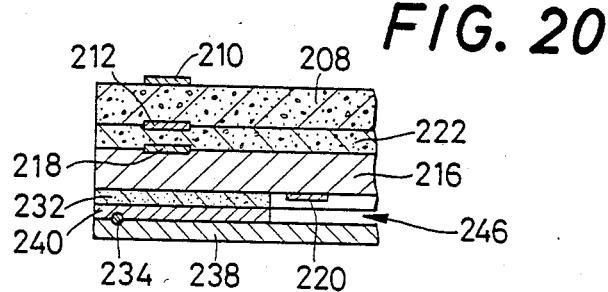
FIG. 20 is a view corresponding to FIGS. 17 and 19, showing a further modified form of an oxygen sensor similar to those of FIGS. 16 and 18.

Although the measuring and reference electrodes 218, 220 of the sensing cell 204 are disposed on the same surface (inner surface) of the gastight solid electrolyte body 216, it is possible that these two electrodes 218, 220 are provided on the opposite surfaces, respectively. An example of such a modification is illustrated in FIG. 20.

In this modified sensor, the reference electrode 220 is disposed on the outer surface of the solid electrolyte body 216 of the sensing cell 204, and exposed to a reference-gas passage 246 which is similar to the passage 246 of the preceding sensor. Described more specifically, the inner ceramic layer 240 of the heater 206 has an elongate cutout (slot) similar to that formed in the spacer member 242 of the preceding sensor, and the outer ceramic layer 238 is adapted to serve as a covering member like the covering member 244 of the preceding embodiment. Further, the electrically insulating layer 232 has a cutout similar to that provided in the ceramic layer 242. With these members 238, 240 and 232 stacked on the outer surface of the solid electrolyte body 216, there is formed the reference-gas passage 246 which is open at one end to the ambient atmosphere, and in which the reference electrode 220 is located such that it is substantially completely protected from exposure to the measurement gas by the gastight ceramic layers 238, 240.

As the other parts of the instant modified form of the sensor are functionally identical to those of the aforementioned sensors, the same reference numerals have been used to identify the corresponding parts, and a repeated detailed description thereof is omitted herein.

As is apparent from the foregoing description, the electrochemical devices of FIGS. 16–20 according to the invention comprise a laminated assembly of electrochemical pumping and sensing cells, and a suitably constructed heater which is disposed on the side of the electrochemical sensing cell. The device is characterized in that the reference electrode exposed to a predetermined reference atmosphere is spaced from the measuring electrode exposed to the controlled atmosphere of the measurement gas, in a plane of vertical elevation perpendicular to the plane of lamination of the device. In this arrangement, the transfer of heat from the heater toward the pumping cell is not hindered by the reference electrode or a portion of the reference-gas passage in the vicinity of the reference electrode, whereby the pumping cell is relatively efficiently heated by the heater, and its pumping ability is held at a higher level, while at the same time the service life of the heater is prolonged. The industrial significance of the third embodiment is found to reside in these advantages, as well as in the previously indicated advantages arising from the co-planar arrangement of the measurement-gas space and the reference-gas space.

While the present invention has been described in its preferred embodiments, and the individual embodiments have been described in several forms, for illustrative purpose only, the electrochemical devices of the invention are not limited to the illustrated details of construction and arrangements; but it will be obvious to those skilled in the art that various changes, modifications and improvements may be made in the invention without departing from the spirit and scope of the invention.

Although the electrochemical devices according to the invention are preferably used as lean-burn sensors as illustrated, the device may be used as a rich-burn sensor for handling a fuel-rich exhaust gas whose oxygen partial pressure is lower than that of the stoichiometric air-fuel ratio, as previously indicated. In this latter instance, the direction of flow of an electric current through the pumping cell is reversed. Further, the electrochemical devices of the invention are equally suitably used as oxygen sensors for detecting exhaust gases which are produced in a combustion process at the stoichiometric air-fuel ratio. In any case, the concentration of oxygen (selected component) of a measurement gas, or the concentration of excess fuel in an exhaust gas is obtained with known methods of measurement. Further, the invention is also embodied as various sensors or controller for determining or controlling the concentration of specific components of a fluid associated with electrode reaction, such as nitrogen, carbon dioxide and hydrogen, other than oxygen.

What is claimed is:

1. An electrochemical device for determining the concentration of a component in a gaseous fluid, comprising:
    a planar solid electrolyte body having a means for defining a reference-gas space in which a reference gas exists;
    a measuring electrode disposed on one surface of said planar solid electrolyte body and exposed to said gaseous fluid;
    a first reference electrode disposed on another surface of said planar solid electrolyte body and exposed to said reference-gas space; and
    a second reference electrode disposed on said another surface of said solid electrolyte body facing said measuring electrode such that said second reference electrode is insulated from direct contact with said reference gas and is electrically connected to said first reference electrode.

2. The electrochemical device of claim 1, wherein said first and second reference electrodes, together with said measuring electrode, comprise a sensing cell.

3. The electrochemical device of claim 1, further comprising a heater layer disposed on one side of said planar solid electrolyte body remote from said one surface thereof.

4. The electrochemical device of claim 1, wherein said solid electrolyte body consists of at least two solid electrolyte layers superposed on each other, said measuring electrode being disposed on an exposed surface of a first of said at least two layers, said first reference electrode being disposed on a surface of a second of said at least two electrodes which is exposed to said reference gas space, and said second reference electrode being embedded between said at least two layers.

5. The electrochemical device of claim 4, wherein said first of said at least two layers includes a slit, and said second of at least two layers includes said another surface on which said first reference electrode is disposed, said slit and said another surface cooperating to define said reference-gas space.

6. The electrochemical device of claim 1, wherein said measuring electrode comprises a pair of measuring of electrode portions and said second reference electrode comprises a pair of second reference electrode portions facing said pair of measuring electrode portions.

7. An electrochemical device for determining the concentration of a component in a gaseous fluid, comprising:
    a planar solid electrolyte body comprising at least two solid electrolyte layers superposed on each other and having a means for defining a reference-gas space in which a reference gas exists;
    a measuring electrode disposed on an exposed surface of a first of said at least two solid electrolyte layers and being exposed to said gaseous fluid;
    a first reference electrode disposed on a surface of a second of said at least two solid electrolyte layers which is exposed to said reference-gas; and
    a second reference electrode embedded between said at least two solid electrolyte layers facing said measuring electrode such that said second reference electrode is insulated from direct contact with said reference gas and is electrically connected to said first reference electrode.

8. The electrochemical device of claim 7, further comprising a heater layer disposed on one side of said planar solid electrolyte body remote from said exposed surface thereof.

* * * * *